United States Patent [19]
Salyer

[11] Patent Number: 5,171,312
[45] Date of Patent: Dec. 15, 1992

[54] TOOL DRIVER

[75] Inventor: Paul E. Salyer, Warsaw, Ind.

[73] Assignee: Othy, Inc., Warsaw, Ind.

[21] Appl. No.: 518,523

[22] Filed: May 3, 1990

[51] Int. Cl.$^5$ .............. A61B 17/00; B25B 21/00
[52] U.S. Cl. ................................ 606/81; 408/124; 81/52; 606/180
[58] Field of Search .......... 606/79, 80, 180, 81, 606/91, 96, 99; 81/52, 53.1, 53.11, 53.12, 467, 472, 473, 474, 475, 478, 480, 482, 58, 58.3, 60, 61, 180.1, 185.2, DIG. 2; 408/125, 126, 131, 153, 160, 161, 164–167, 171, 185

[56] References Cited

U.S. PATENT DOCUMENTS

| | | | |
|---|---|---|---|
| 502,060 | 7/1893 | Williams | 81/DIG. 2 |
| 2,357,105 | 8/1944 | Grinnell | 81/53.11 |
| 4,131,116 | 12/1978 | Hedrick | 606/81 |
| 4,611,587 | 9/1986 | Powlan | 606/81 |
| 4,716,894 | 1/1988 | Lazzeri et al. | 606/99 |

Primary Examiner—Stephen C. Pellegrino
Assistant Examiner—Glenn Dawson
Attorney, Agent, or Firm—Lundy & Associates

[57] ABSTRACT

A tool driver comprising a shaft, a shank, a flange, a clamp and a retainer. The shaft has a longitudinal axis and opposed ends. The shank is joined to one end of the shaft. The flange is joined to the other end of the shaft and has an outwardly facing flange surface extending from the shaft transversely of the axis. The clamp has a clamping surface facing the flange surface. The clamp is movable axially relative to the flange to vary the separation of the surfaces. The retainer is operatively connected to the clamp and is movable relative to the clamp between a first position and a second position. The retainer, in the first position, precludes relative movement of the clamp and the flange.

29 Claims, 4 Drawing Sheets

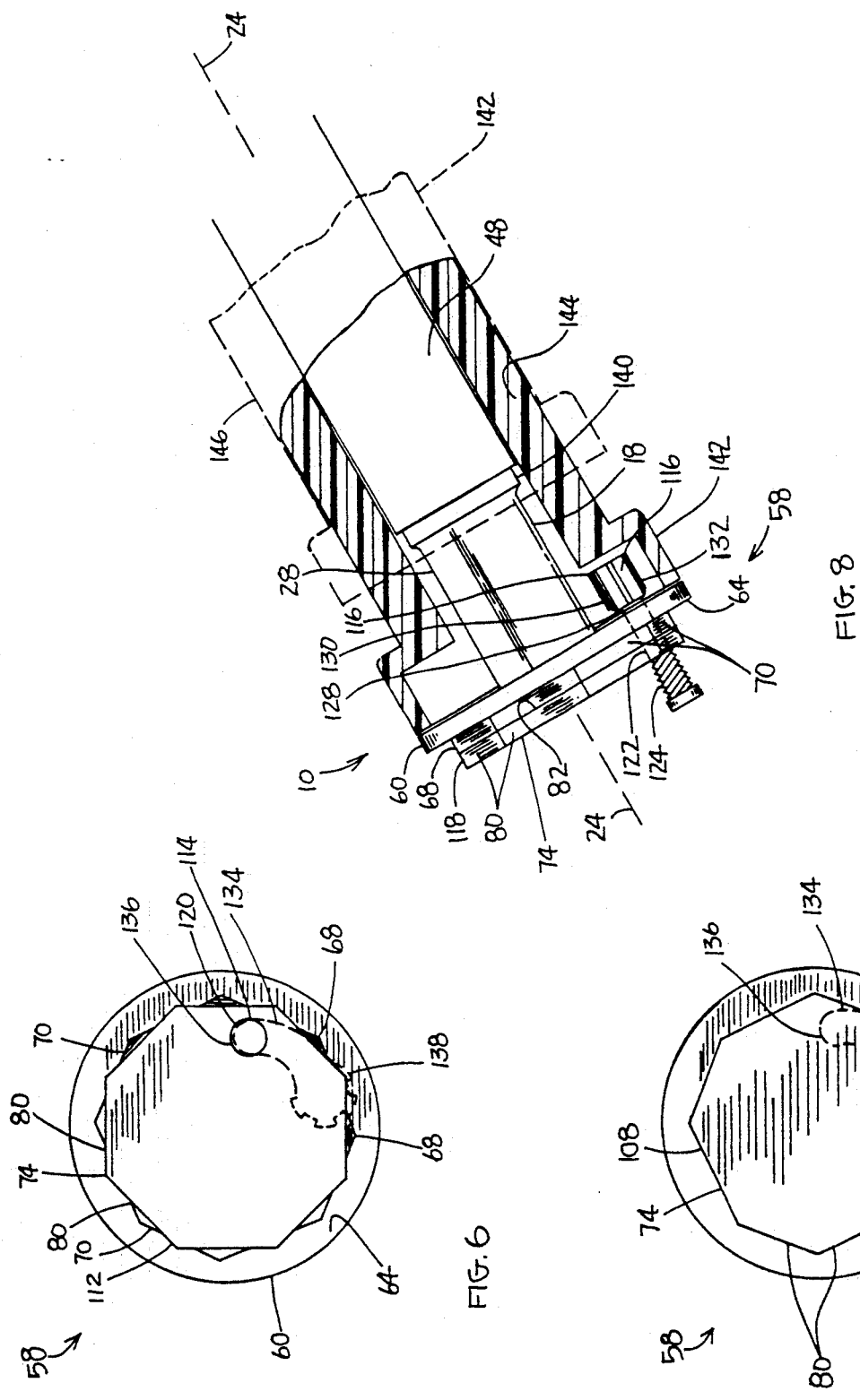

TOOL DRIVER

BACKGROUND OF THE INVENTION

The present invention pertains to attachments for holding rotary tools and more particularly pertains to a tool driver suitable for use with an acetabular reamer cup or other similarly driven tool.

Acetabular reamer cups are surgical tools, which are used to cut hemispherical cavities in pelvis bones for the insertion of artificial hip joints. The acetabular reamer cups are mounted on tool drivers, which in turn are mounted in the chuck or collet of a portable drill or flexible powered shaft. Acetabular reamer cups are separable from their tool drivers for replacement purposes because it is difficult to sharpen or clean acetabular reamer cups. It may be necessary to change cups during an operation. Appropriate tool drivers are not inexpensive and must be reused.

Previous tool drivers usable with acetabular reamer cups grip the cup by means of a flange and slot and an opposed spring-loaded ball catch, like that on a socket wrench or socket driver. This presents a problem in that crack, crevices and intracately shaped parts tend to trap dried blood, which is very difficult to remove during cleaning. An additional problem is that unless tolerances of cups and tool drivers are made very close, at increased cost, there may be considerable free play between a cup and its tool driver. This increases wear and decreases the precision of the tool.

A tool driver for an acetabular reamer cup is subject to a number of restrictions. Due to the environment in which acetabular reamer cups are used, their interiors must be readily accessible for cleaning. This necessitates a large opening on the underside of each cup and eliminates methods of attaching the cup to a tool driver, which would block the underside. It is also best to minimize weight of the acetabular reamer, since surgeons must use it as a delicate instrument. This eliminates methods of attaching the cup to a tool driver, which tend to increase total tool weight. It is also best to eliminate interior angles of ninety degrees or less, within the cups to decrease contamination. This may require a cup which has a base that is convex rather than planar. Such a cup cannot be used with tool drivers that cannot tightly grip a curved surface. It is also best to minimize contamination, to have the acetabular reamer easily disassembleable into a small number of unitary parts for cleaning.

It is therefore highly desirable to provide an improved tool driver.

It is also highly desirable to provide an improved tool driver which can tightly grip and easily release an acetabular reamer cup.

It is also highly desirable to provide an improved tool driver, which does not have a large number of intricately shaped parts, cracks, crevices, or small angles.

It is also highly desirable to provide an improved tool driver which is lightweight and can tightly grip a tool having a base which is curved and surrounds a large opening.

It is also highly desirable to provide an improved tool driver which can be quickly and completely disassembled into a small number of pieces for cleaning.

It is finally highly desirable to provide an improved tool driver which meets all of the above desired features.

SUMMARY OF THE INVENTION

It is an object of the invention to provide an improved tool driver.

It is another object of the invention to provide an improved tool driver which can tightly grip and easily release an acetabular reamer cup.

It is another object of the invention to provide an improved tool driver, which does not have a large number of intricately shaped parts, cracks, crevices, or small angles.

It is another object of the invention to provide an improved tool driver which is lightweight and can tightly grip a tool having a base, which is curved and surrounds a large opening.

It is another object of the invention to provide an improved tool driver which can be quickly and completely disassembled into a small number of pieces for cleaning.

It is finally an object of the invention to provide an improved tool driver which meets all of the above desired features.

In the broader aspects of the invention there is provided a tool driver comprising a shaft, a shank, a flange, a clamp and a retainer. The shaft has a longitudinal axis and opposed ends. The shank is joined to one end of the shaft. The flange is joined to the other end of the shaft and has an outwardly facing flange surface extending from the shaft transversely of the axis. The clamp has a clamping surface facing the flange surface. The clamp is movable axially relative to the flange to vary the separation of the surfaces. The retainer is operatively connected to the clamp and is movable relative to the clamp between a first position and a second position. The retainer, in the first position, precludes relative movement of the clamp and the flange.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 6 is a front plan view of an alternative embodiment of the tool driver of the invention. The slot and flange are shown by dashed lines. The clamp and a retainer are shown in an engaged position.

FIG. 7 is a front plan view of the tool driver of FIG. 6. The slot and flange are shown by dashed lines. The clamp and a retainer are shown in a disengaged position.

FIG. 8 is a cut-away, partial side plan view of the tool driver of FIG. 6. The threaded hole in the clamp is indicated by dashed lines. The glove protector shield is shown in a normal position in solid lines and in a retracted position in dashed lines. The clamp and a retainer are shown in a retracted position.

DESCRIPTION OF A SPECIFIC EMBODIMENT

Figure 1:
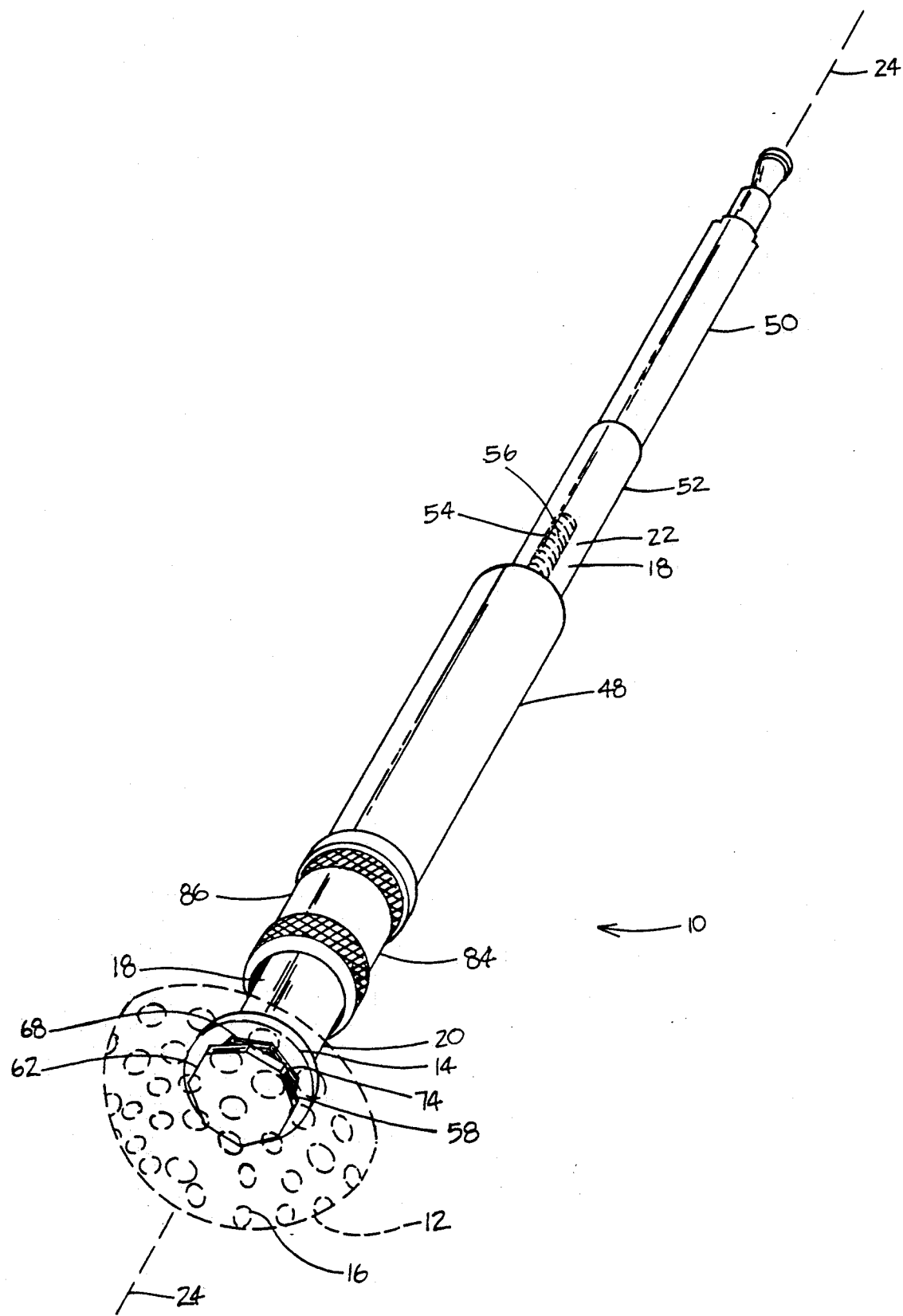
FIG. 1 is a perspective view of an embodiment of the tool driver of the invention and an acetabular reamer cup, held by the tool driver, indicated by dashed lines. Engaged threads on a shaft and a shank are also indicated by dashed lines.

Referring to FIG. 1, the tool driver 10 of the invention holds an acetabular reamer cup or tool 12, which has a base 14 and a cutting surface 16. Tool driver 10 has an elongated shaft 18, which has opposed front and rear ends 20, 22 and a longitudinal axis 24.

Figure 2:
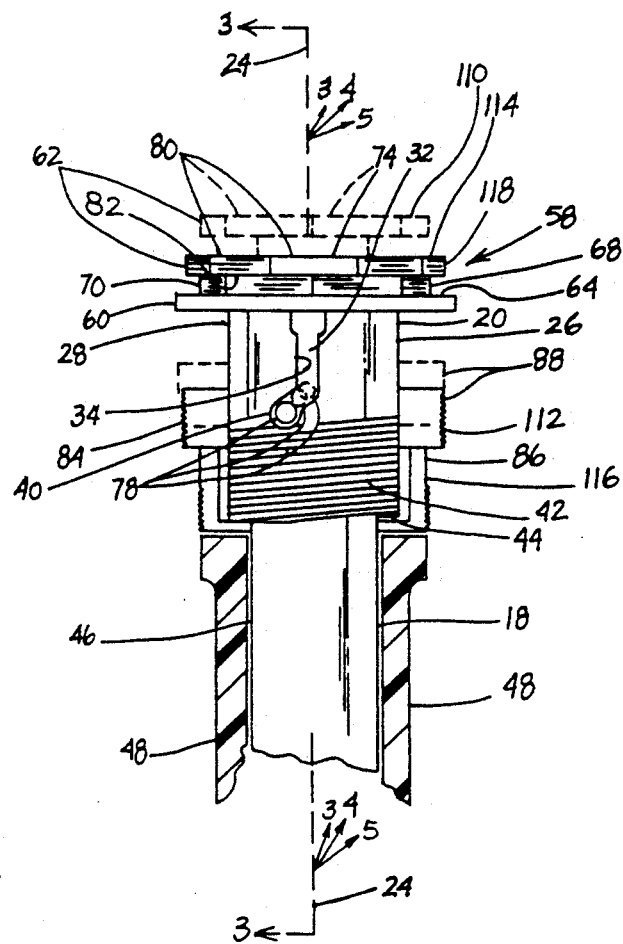
FIG. 2 is a cut-away partial side plan view of the tool driver of FIG. 1. A retainer and clamp are shown in retracted positions in solid lines and in engaged and disengaged positions in dashed lines.
Figure 3:
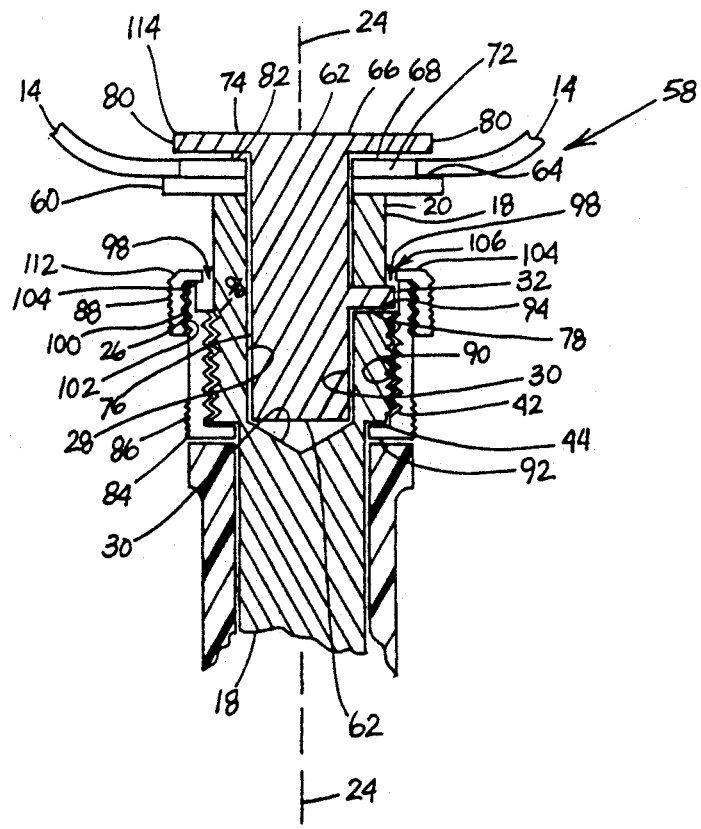
FIG. 3 is a partial cross-sectional view of the tool driver of FIG. 2 taken along section line 3—3. The retainer and clamp are shown in engaged positions.

Referring now to FIGS. 2 and 3, shaft 18 has a front section 26, which has a cylindrical shaft wall 28 surrounding a longitudinal bore 30, extending longitudinally from front end 20. Bore 30 is smooth and cylindrical. Extending through shaft wall 28 and communicating with bore 30 is a slot 32, which is bordered by a slot surface or cam surface 34. Slot 32 extends in from front end 20, initially parallel to axis 24 and then extends part-way around and down front section 26 to a slot bottom or stop 40. Shaft 18 has external threads 42 to the rear of slot 32. The handedness of external threads 42, that is the direction of rotation for tightening, is the same as the direction of rotation of tool driver 10 during use, as determined by the handedness of a particular tool 12. External threads 42, to the rear, have an edge or stop 44, which is generally perpendicular to axis 24 and behind which the diameter of rear section 46 of shaft 18 is reduced.

Referring now to FIGS. 1 and 2, a generally cylindrical glove protector or sleeve 48 loosely encircles rear section 46 of shaft 18 and can freely rotate, relative to shaft 18, about axis 24. In a particular embodiment of the invention, glove protector 48 is a material such as nylon, which provides low frictional resistance, without lubrication.

Referring now to FIG. 1, a shank 50 is joined to shaft 18 at rear end 22. Shank 50 is mostly cylindrical in cross-section and is coaxial with shaft 18. Shank 50 has a band 52, adjacent to shaft 18, which has a diameter larger than the internal diameter of sleeve 48. Shank 50 and rear end 22 of shaft 18 are removably secured together. In a particular embodiment of the invention, that connection is provided by reciprocal threads 54, 56 on rear end 22 of shaft 18 and on shank 50. The handedness of threads 54, 56 is the same as that of threads 42 of shaft 18.

Referring now to FIGS. 2 and 3, at front end 20 of shaft 18 is a tool holder 58, which includes a flange 60, fixed relative to shaft 18, and a movable clamping member 62. Flange 60 has a flange surface 64, which is roughly annular in shape and receives tool base 14. Flange surface 64 extends radially outward from shaft 18 and faces axially outward and forward from shaft 18 and flange 60. A hole 66 in flange surface 64 communicates with slot 32 and bore 30. In a particular embodiment of the invention, flange surface 64 is smaller in diameter than base 14.

Referring now to FIG. 3, flange 60 has a boss 68, which extends axially outward from flange surface 64. Edges 70 of boss 68, adjoining flange surface 64, have an axial dimension, which is the same or smaller than the thickness of tool base 14. Boss 68 and tool base 14 are complementary in shape, such that boss 68 is interposable in and has the same shape, in cross-sections perpendicular to axis 24, as an opening 72 in base 14. Boss edges 70 closely receive base 14, when base 14 engages flange surface 64.

Referring now to FIGS. 1 and 2, boss 68 has generally the shape of polygonal prism. In a particular embodiment of the invention, boss 68 has the shape of a regular octagonal prism.

Figure 4:
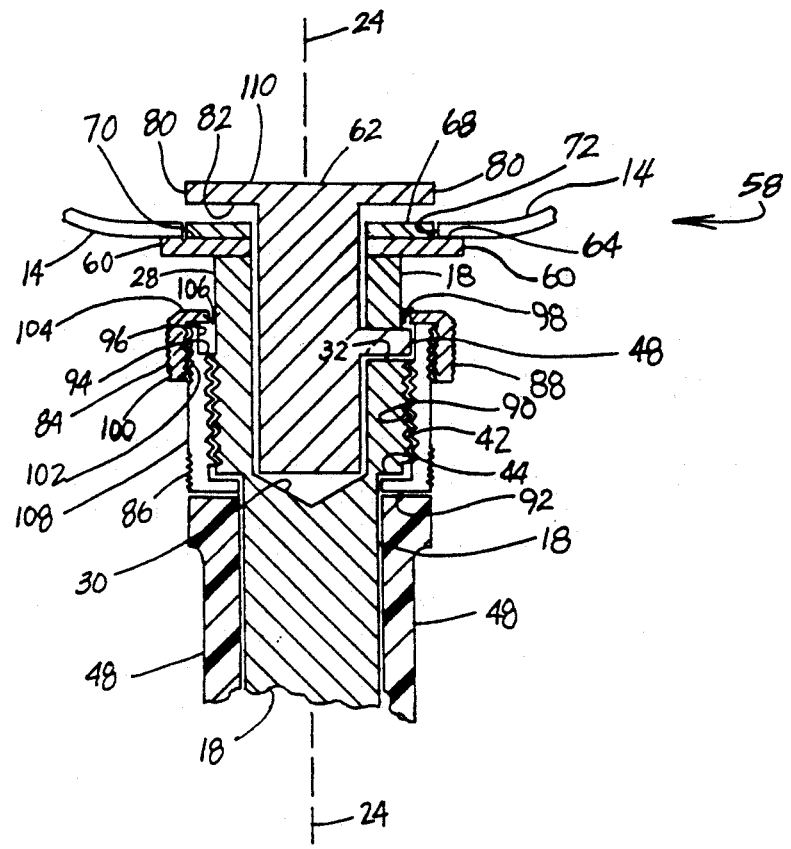
FIG. 4 is a partial cross-sectional view of the tool driver of FIG. 2 like FIG. 3. The retainer and clamp are shown in disengaged positions.
Figure 5:
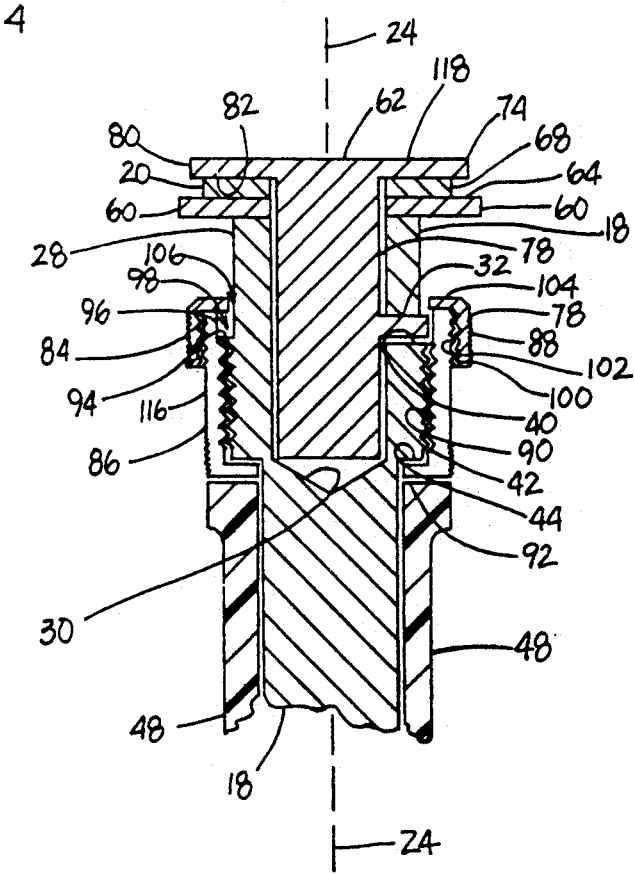
FIG. 5 is a partial cross-sectional view of the tool driver of FIG. 2 like FIG. 3. The retainer and clamp are in retracted positions.

Referring now to FIGS. 3, 4, and 5, clamping member 62 is unitary and has a clamp 74, a rod 76 and a pin or follower 78. Clamp 74 is exterior to flange 60 and movable relative to flange 60 and shaft 18. Clamp 74 and tool base 14 are complementary in shape, such that edges 80 of clamp 74 are interposable in opening 72 and clamp 74 has the same shape, in cross-section perpendicular to axis 24, as opening 72. In a particular embodiment of the invention, clamp edges 80 and boss edges 70 have identical dimensions. Clamp 74 has a clamping surface 82, which faces rearward, toward flange surface 64. In a particular embodiment of the invention, clamping surface 82 and flange surface 64 are both planar.

Rod 76 extends generally perpendicularly from clamping surface 82. Rod 76, clamp 74, flange 60, and shaft 18 are all coaxial. Rod 76 is positioned in and generally complementary in shape to bore 30 and is slideable within bore 30. Pin 78 extends from rod 76 out through slot 32 in shaft 18. Pin 78 is sized so as to fit loosely in slot 32. Rotational and axial movement of rod 76 in bore 30 is limited by the travel of pin 78 in slot 32.

A retainer 84, which has a retainer body 86 and a retainer ring 88, is disposed on shaft 18 to the rear of flange 60. Body 86 has internal threads 90, which are reciprocal to and engaged with threads 42 of shaft 18. To the rear of internal threads 90 is an endplate 92, which closely surrounds shaft 18. At the forward end of internal threads 90, body 86 is stepped outward, forming an internal body rim 94 and a cylindrical forward wall 96, of increased internal diameter. Forward wall 96 encircles a cylindrical cavity 98, into which pin 78 extends. Pin 78 does not engage forward wall 96, since the internal radius of forward wall 96, that is, the radius of cavity 98, is greater than the radius of front section 26 of shaft 18 plus the extension of pin 78 beyond shaft 18. Forward wall 96 has external threads 100, which are opposite in handedness to internal threads 90. In a particular embodiment of the invention, body 86 is externally knurled to the rear of external threads 100.

Ring 88 has internal threads 102, which are reciprocal to and engaged with external threads 100 of body 86. Above internal threads 102, ring 88 has a ring rim 104, which defines a ring rim opening 106, through which shaft 18 extends. The internal diameter of ring 88, that is, the diameter of ring rim opening 106, is larger than the diameter of front section 26 of shaft 18 plus the extension of pin 78 beyond shaft 18. The internal radius of ring 88, that is, the radius of ring rim opening 106, is smaller than the radius of front section 26 of shaft 18 plus the extension of pin 78 beyond shaft 18. Ring rim 104 and body rim 94 loosely grip pin 78, from forward and behind, respectively. In a particular embodiment of the invention, ring 88 is externally knurled.

Referring now to FIGS. 2, 3, 4, and 5, retainer 84 and engaged pin 78 are selectably movable in relation to shaft 18, by rotation of retainer 84 relative to shaft 18. That rotation changes the engagement of shaft and retainer threads 42, 90 and translates retainer 84 axially along shaft 18. Movement of retainer 84 relative to shaft 18 drives engaged pin 78 axially and slides pin 78 along slot 32, pivoting pin 78 relative to axis 24. The motion of pin 78 rotates and axially slides rod 76 within bore 30 and alters the separation and rotational alignment of flange surface 64 and clamping surface 82.

Retainer 84 and clamp 74 are movable between disengagement positions 108, 110, shown in FIGS. 2 and 4, past engagement or clamping positions 112, 114, shown in FIGS. 2 and 3, to retracted positions 116, 118, shown in FIGS. 2 and 5. In disengagement position 110, clamping and flange surfaces 82, 64 are at a maximum separation and are rotationally aligned, that is, each clamp edge 80 is coplanar with a respective boss edge 70. In engagement position 114, clamping and flange surfaces 82, 64 are separated by the thickness of tool base 14. Clamping and flange surfaces 82, 64 are out of alignment in engagement and retracted positions 114, 118. In a particular embodiment of the invention, in retracted position 118, clamping and flange surfaces 82, 64 are contiguous and maximally offset from rotational alignment. In a particular embodiment of the invention in which boss 68 and clamp 74 define regular polygons, in retracted position 118, edges 70, 80 are offset by one-half the angle of a sector defined by an edge.

Rotation of retainer 84 beyond disengagement and retracted positions 108, 116 is constrained. Referring now to FIG. 4, in disengagement position 108, endplate 92 of retainer body 86 engages edge 44 of upper section of shaft 18, precluding further forward motion. Referring now to FIG. 5, in retracted position 116, pin 78 is tightly gripped by ring rim 104 and bottom 40 of slot 32, precluding further rearward motion.

Referring now to FIGS. 2-5, in use, retainer 84 is grasped by an operator and rotated relative to shaft 18, in a direction of rotation that causes retainer 84 to move axially forward. That rotation is continued until retainer 84 is in disengagement position 108 and will rotate no further. If the inappropriate direction of rotation is chosen, that will become rapidly apparent when retainer 84 assumes retracted position 116 and stops rotating. Once retainer 84 is in disengagement position 108, clamp and flange surfaces 82, 64 are in registry, such that clamp and boss edges 80, 70 are aligned and a tool 12 may then be placed on tool driver 10, by moving tool 12 axially and sequentially interposing clamp 74 then boss 68 within opening 72 of tool base 14. In a particular embodiment of the invention, the separation of clamping and flange surfaces 82, 64, in disengagement position 110, as determined by the axial separation of edge 44 and slot bottom 40, is less than the thickness of tool base 14, so that it is not possible for the operator to inadvertently position tool base 14 between clamp 74 and boss 68, during assembly.

Next, with tool base 14 held in engagement with flange surface 64 by gravity or other means, retainer 84 is grasped and rotated so as to move axially rearward. That rotation is continued until retainer 84 will rotate no further. Clamp 74 and retainer 84 are then in engagement positions 114, 112, tool base 14 is gripped between clamping and flange surfaces 82, 64 and respective clamping and boss edges 80, 70 are axially offset. Retainer 84 is locked or set in position by the engagement of threads 42, 90. Tool base 14 is contacted uniformly, all around tool base 14. Since tool base 14 is contacted only adjacent to opening 72, curvature or non-uniformity of tool base 14, distal to opening 72, does not effect engagement of base 14 by tool driver 10.

After tool 12 is attached, tool driver 10 may then be chucked to a rotary drill or the like (not shown) and the tool 12 utilized. Glove protector 48 may be gripped by the operator during use without risk of catching surgical gloves or the like, since shaft 18 rotates freely within glove protector 48. Band 52 of shank 50 and retainer 84 limit axial movement of sleeve 48, so that shaft 18 cannot shift back and forth within sleeve 48.

It is unnecessary to use a wrench or the like to tighten clamp 74 against boss 68, since the shapes of boss 68 and tool opening 72 are non-circular and rotation of tool 12 independent of shaft 18 is thus precluded. In addition, retainer 84 is threaded such that contact of an immobile object with retainer 84 during use will tend to cause retainer body 86 to tighten on shaft 18 or retainer 84 to tighten on retainer body 86.

During use, tools 12 may be interchanged readily and quickly with disassembly of tool driver 10. After use, disassembly for cleaning is quick and complete. Tool 12 is removed, then threadedly engaged parts are unscrewed. Shank 50 and shaft 18 are disassembled and glove protector 48 is slid off. Ring 88 is unscrewed from retainer body 86, which can then be unscrewed and slid off shaft 18. Ring 88 is then offset from axis 24 and slipped past pin 78 and off shaft 18. Clamping member 62 may then be lifted free, completely separating tool driver 10 into unitary pieces for cleaning.

Referring now to FIGS. 6, 7, and 8, in another alternative embodiment of the invention, a through flange retainer 120 replaces retainer 84. In this embodiment of the invention, clamp 74 has a threaded hole 122 and retainer 120 has a threaded section 124, which is reciprocal to and engaged with threaded hole 122, and has a stop 126, which is forward of hole 122 and is larger than hole 122. Rearward of threaded section 124 is a sloped neck 128 and then a head 130. The shape of head 130 is roughly that of a cylinder larger in diameter than threaded section 124. Head 130 has a series of longitudinal grooves 132, which are not uniform in depth.

Flange 60 has a slot 134 through which threaded section 124 of retainer 120 axially extends. Slot 134 curves partway around flange 60 and is countersunk at a first end 136 to receive and hold neck 128, when retainer 120 is tightened. Slot 134, at a second end 138, is complementary in shape to head 130. Movement of retainer 120 along slot 134, rotates retainer 120 and clamp 74 about axis 24 and varies the rotational alignment of clamp 74 and boss 68. Moving retainer 120 axially, by changing engagement of threaded section 124 and threaded hole 122, alters the separation of clamp surface 82 and flange surface 64.

Like the previously disclosed embodiment of the invention, retainer 120 and clamp 74 are movable between disengagement positions 108, 110, engagement positions 112, 114 and retracted positions 116, 118, all respectively. In disengagement position 110, clamping and flange surfaces 82, 64 are rotationally aligned and are freely movable relative to each other. In disengagement position 108, retainer 120 is rotated, in hole 122, maximally rearward, and clamp 74 and retainer 120 are rotated relative to axis 24, so that retainer 120 occupies second end 138 of slot 134. Clamping member 62, remains attached to flange 60, unless retainer head 130 is pulled through second end 134. In engagement and retracted positions 114, 118, clamping and flange surfaces 82, 64 are rotationally offset and retainer neck 128 is tightly threaded against first end 136 of slot 134.

Shaft 18 has a solid shaft wall 28 and, below retainer 120, an annular protrusion 140, which adjoins sleeve 48 and has a diameter larger than the internal diameter of sleeve 48. A glove protector shield 142 encircles and slideably grips sleeve 48. Shield 142 is movable axially of shaft 18, between a normal position 144, in which shield 142 engages flange 60 and covers retainer 120 and a retracted position 146, in which retainer 120 is accessible.

By the invention, an improved tool driver is provided which can tightly grip and easily release an acetabular reamer cup which can be easily disassembled and assembled for cleaning and use. The tool driver has not spring loaded catches and can easily be cleaned after use.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a shaft having a longitudinal axis and opposed ends, a flange disposed at one end of said shaft, said flange having a flange surface, said flange extending outwardly from said shaft transversely of said axis, a clamping member on said shaft, said clamping member having a clamping surface facing said flange surface, said clamping member being movable axially relative to said flange to vary the separation of said surfaces, a retainer on said shaft operatively connected to said clamping member for actuating said clamping member, said retainer being rotatable about said shaft between an engagement position and a disengagement position to move said clamping surface into and out of clamping relation with said flange surface, said retainer in said engagement position corresponding to said clamping and flange surfaces in said clamping relation and said retainer in said disengagement position corresponding to said clamping and flange surfaces in a spaced relation.

2. The tool driver of claim 1 wherein movement of said retainer between said disengagement position and said engagement position moves said clamping member between a disengagement position and an engagement position.

3. The tool driver of claim 2 wherein said disengagement positions of said retainer and said clamping member are rotated about said axis from said engagement positions.

4. The tool driver of claim 3 wherein said disengagement positions are displaced axially from said engagement positions.

5. The tool driver of claim 1 wherein said shaft has a bore extending longitudinally into said shaft at the same end as said flange and wherein said clamping member has a rod extending generally perpendicularly from said clamping surface, said rod being slideable within said bore.

6. The tool driver of claim 1 wherein said shaft has a cam surface and said clamping member has a follower and wherein movement of said retainer between said disengagement position and said engagement position drives said follower along said cam surface.

7. The tool driver of claim 6 wherein said cam surface extends partially around said shaft.

8. The tool driver of claim 1 wherein said retainer is movable between said engagement position and said disengagement position and wherein said shaft has stops disposed to arrest movement of said retainer at said engagement position and at said disengagement position.

9. The tool driver of claim 1 wherein said flange has a boss extending axially outwardly from said flange surface and wherein said clamping member has a clamp, said clamp including said clamping surface, said clamp having a shape in cross-section taken transversely of said axis interposable on a cross-section of said boss taken in the same direction.

10. The tool driver of claim 9 wherein said clamp and boss cross-sections are substantially identical and each have the shape of a regular polygon.

11. A tool driver comprising a shaft having a longitudinal axis and opposite ends, said shaft having a bore extending from one of said ends toward the other of said ends, a shank joined to the other end of said shaft as said bore, a tool holder disposed at said one end of said shaft, said tool holder having a flange at said one end, said flange adapted to support a tool driven by said tool driver, said flange having an outwardly facing flange surface, said flange extending from said shaft transversely of said axis, a clamping member having a clamping surface and a rod extending generally perpendicularly from said clamping surface, said rod being positioned and slideably movable in said bore to place said clamping surface into and out of registry with said flange surface, and a retainer operatively connected to said clamping member, said retainer being movable relative to said shaft to move said clamping surface relative to said flange surface into and out of clamping relation with said flange surface.

12. The tool driver of claim 11 further comprising a boss extending from said flange axially outwardly of said shaft, said boss being adapted to being placed within an opening in the base of a tool.

13. The tool driver of claim 12 wherein said boss has a thickness dimension axially of said shaft which is less than the thickness of said tool base.

14. The tool driver of claim 12 wherein said boss is adapted to be placed in an opening in the base of a tool having a shape complementary to said boss whereby said tool is prevented from rotating independently of said shaft.

15. The tool driver of claim 12 wherein said clamping member is adapted to be inter-positionable in an opening in the base of a tool when out of clamping relation with said flange and non-interpositionable in an opening in the base of a tool when in a clamping relationship with said flange.

16. The tool driver of claim 12 wherein said clamping member and said boss have substantially the same shape in cross-section taken transversely of said shaft axis.

17. The tool driver of claim 11 wherein said retainer slides said rod axially of said shaft and rotates said clamping member in relation to said shaft.

18. The tool driver of claim 11 wherein said shaft and said bore define a shaft wall, said shaft wall having a slot therein, said clamping member having a pin extending from said rod, said pin being positioned in said slot, said bore and said pin guiding the movement of said clamping member in relation to said shaft.

19. The tool driver of claim 18 wherein said pin extends from said shaft when in said slot, and said retainer engages a portion of said pin extending from said shaft when said pin in said slot, said retainer being selectably movable in relation to said shaft in engagement with said pin thereby to move said clamping member in relation to said shaft.

20. The tool driver of claim 19 wherein said retainer is lockable against movement relative to said shaft.

21. The tool driver of claim 19 wherein said retainer includes a body threadedly engaged to said shaft, said body being movable in relation to said shaft by rotation of said body relation to said shaft.

22. The tool driver of claim 21 wherein said body and said shaft are engaged by threads having the same handedness as the intended direction of rotation of said shaft.

23. The tool driver of claim 19 wherein said retainer extends axially through said flange and engages said clamping member, said retainer being movable transversely of said shaft and rod to move said clamping member into and out of said clamping relation.

24. The tool driver of claim 23 wherein said retainer rotates as said retainer moves transversely of said shaft.

25. The tool driver of claim 24 wherein said retainer is threadedly engaged with said clamping member whereby said clamping member rotates when said retainer rotates.

26. The tool driver of claim 19 wherein said shaft and said shank are removably connected coaxially.

27. A tool driver comprising a shaft having a longitudinal axis and opposite ends, said shaft having a bore extending from one of said ends toward the other of said ends, a shank joined to said other end of said shaft, a glove protector slideably positioned on said shaft, said glove protector being movable coaxially of said shaft independent of said shaft, a tool holder disposed at said one end of said shaft, said tool holder having a flange, said flange having an outwardly facing flange surface, said flange extending from said shaft transversely of said axis, a clamping member having a clamping surface and a rod extending generally perpendicularly from said clamping surface, said rod being positioned and slideably movable in said bore to place said clamping surface in and out of registry with said flange surface, and a retainer on said shaft operatively connected to said clamping member, said retainer being movable relative to said shaft to move said clamping surface relative to said flange surface.

28. The tool driver of claim 27 wherein said glove protector includes a shield movable axially of said shaft, said shield being movable relative to said flange between a normal position, in which said glove protector engages said flange, and an access position, in which said glove protector is spaced apart from said flange.

29. The tool driver of claim 27 wherein said shaft and said shank are threadedly secured together by threads having the same handedness as the direction of rotation of said shaft.

* * * * *